United States Patent [19]

Cavazza

[11] 4,443,475

[45] Apr. 17, 1984

[54] AMIDES OF ACYL-CARNITINES, PROCESS FOR PREPARING SAME AND PHARMACEUTICAL COMPOSITIONS CONTAINING SUCH AMIDES

[76] Inventor: Claudio Cavazza, 35, Via Marocco, 00144 Rome, Italy

[21] Appl. No.: 382,275

[22] Filed: May 26, 1982

Related U.S. Application Data

[63] Continuation of Ser. No. 142,504, Apr. 21, 1980, abandoned.

[30] Foreign Application Priority Data

Apr. 23, 1979 [IT] Italy ............................. 48816 A/79

[51] Int. Cl.³ ...................... A61K 31/23; C07C 103/54
[52] U.S. Cl. .................................. 424/311; 424/312;
  560/169; 560/170; 560/179; 560/178; 560/147;
  560/251; 560/226; 560/45; 260/404.5
[58] Field of Search ................. 560/169, 226, 45, 147,
  560/251, 179, 178, 170; 260/404.5; 424/311, 312

[56] References Cited

U.S. PATENT DOCUMENTS 4,032,641  6/1977  Chibata et al. ..................... 424/266

FOREIGN PATENT DOCUMENTS 2388556 11/1978 France .
37-5174  6/1962 Japan .
38-24    1/1963 Japan .

OTHER PUBLICATIONS

Riunite, Chem. Abst., vol. 92, #215769(t), (1980).
Mino et al., Chem. Abst., vol. 77, #151495(f), (1972).
Strack et al., Chem. Abst., vol. 64, #19398(f), (1966).

Primary Examiner—James H. Reamer
Attorney, Agent, or Firm—Ladas & Parry

[57] ABSTRACT

Novel amides of acyl-carnitines having general formula

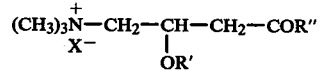

wherein R' is acetyl, propionyl, butyryl (unsubstituted or halogen-substituted) isobutyryl, β-hydroxybutyryl, acetoacetyl, pantothenyl, and linoleyl, and R" is either an unsubstituted amino radical (provided that R' is ather than acetyl) or a substituted amino radical, are therapeutically effective in treatment of functional arrythmias or arrhythmias secondary to myocardialsclerotic diseases and as psychosti-mulants.

7 Claims, No Drawings

AMIDES OF ACYL-CARNITINES, PROCESS FOR PREPARING SAME AND PHARMACEUTICAL COMPOSITIONS CONTAINING SUCH AMIDES

This is a continuation, of application Ser. No. 142,504 filed Apr. 21, 1980, now abandoned.

The present invention relates to a novel class of amides of acyl-carnitines, the processes for preparing same and the pharmaceutical compositions containing such amides.

More particularly, the present invention relates to amides of acyl-carnitines represented by the general formula (I):

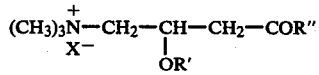

wherein $X-$ is a halogen anion, preferably $Cl-$; R' is: acetyl; halogen-substituted acetyl (e.g. chloroacetyl, dichloroacetyl, bromo-acetyl and the like); propionyl; halogen-substituted propionyl (e.g. bromopropionyl); butyryl; halogen-substituted butyryl (e.g. chlorobutyryl); isobutyryl; β-hydroxy butyryl; acetoacetyl, linoleyl and panthothenyl; and R" is: amino (provided that R' is not acetyl), 2-sulfonyl ethylamino, (2-hydroxy-3-carbethoxy-propyl) amino, (1-carbomethoxy-2-methyl-propyl) amino, (1-carbomethoxy-3-methyl-n-butyl) amino, (1-carbomethoxy-2-methyl-n-butyl) amino, (1,2-dicarbomethoxy-ethyl) amino, (1,3-dicarbomethoxypropyl) amino, (α-carbethoxy-benzyl) amino, (4-carbethoxyphenyl) amino, (2-mercapto-1-carbomethoxy-ethyl) amino, 2-mercaptoethyl amino, (5-trimethyl ammonium choride-1-carbethoxy pentyl) amino, (carbethoxy methyl) amino and (carbethoxy ethyl) amino radicals.

It has been found that the compounds of the present invention have interesting pharmacologic properties and therefore can exhibit useful therapeutic applications.

In particular:

The amides of formula (I) have shown to be endowed with activity stimulating the central nervous system and capable of lowering the convulsive threshold.

Therefore, the therapeutic applications comprise
(a) the treatment of functional arrhythmias or arrhythmias secondary to myocardial-sclerotic diseases unaccompanied by insufficiency of myocardial contractility;
(b) the treatment of depression, as cerebral psychostimulants and as antagonists of barbiturate-induced depression.

In accordance with the invention, the amides of formula (I) are prepared by following two distinct synthesis routes, depending on whether either the acyl-derivative of carnitine is halogenated thus converting it into the corresponding acid halogenide and this latter compound is then condensed with the desired amine or aminoacid (Process A), or the carnitine acyl-derivative is directly condensed with the amine or aminoacid in the presence of a suitable condensing agent (Process B).

More specifically, the Process A comprises the following steps:
(a) adding to a solution of carnitine in a solvent selected from the group consisting of organic acids and the corresponding anhydrides, an acyl halogenide of formula R'X wherein R' has the aforementioned meaning and X is a halogen atom, and keeping the temperature of the mixture thus obtained at about 15°-60° C. for about 4-48 hours, thus obtaining the corresponding acyl-derivative of carnitine;
(b) isolating the acyl-derivative of carnitine by adding to the mixture of step (a) a precipitating agent and purifying by repeated crystallizations;
(c) reacting the acyl-derivative of carnitine of step (b) with an excess of a halogenating agent at about 25°-60° C. for about 0.3-24 hours and remove the excess of halogenating agent, thus obtaining the corresponding acid halogenide of the acyl-derivative of carnitine;
(d) dissolving the acid halogenide of the acyl-derivative of carnitine of the step (c) in an anhydrous inert solvent;
(e) condensing said acid halogenide of the acyl-derivative of carnitine with an organic base selected among the esters of aminoacids with lower aliphatic alcohol having from 1 to 4 carbon atoms, and the amines having formula R"H, wherein R" has the aforementioned meaning, dissolved in an anhydrous inert solvent, keeping the resulting mixture under stirring at room temperature for about 6-48 hours, thus obtaining the amide of formula (I); and
(f) isolating the amide of formula (I) by concentrating the mixture of step (e) and purifying through repeated crystallizations.

The aminoacid ester of step (e) is obtained by esterifying the aminoacid preferably with methanol, ethanol or isopropanol in the presence of gaseous HCl. The ester is then isolated as ester hydrochloride. Subsequently:
(i) the ester hydrochloride is dissolved in $H_2O$, the pH is brought to neutrality with a saturated basic solution, e.g. a $Na_2CO_3$ solution, the solution thus obtained is repeatedly extracted with methylene chloride or chloroform or ethyl ether, the organic phase is concentrated and the aminoacid ester is isolated as free base and used as such for the reaction with the halogenide of the carnitine acyl-derivative; alternatively:
(ii) the ester hydrochloride is suspended in ethyl ether and an equimolar amount of triethylamine or pyridine is added thereto at 0° C.; the thus formed triethylamine or pyridine hydrochloride is filtered off, the ether solution is concentrated and the aminoacid ester isolated as free base is used as such for the reaction with the halogenide of the carnitine acyl-derivative.

According to Process B, after the previously illustrated steps (a) and (b), the following steps are carried out, which comprise:
(c') condensing the acyl-derivative of carnitine of the step (b) in an aqueous solution with an organic base selected among the esters of aminoacids with lower aliphatic alcohols having from 1 to 4 carbon atoms and the amines of formula R"X wherein R" has the aforementioned meaning, in solution of organic solvents in the presence of a solution in an organic solvent of dicyclohexylcarbodiimide, keeping the mixture thus obtained under stirring at room temperature for 2-24 hours, thereby obtaining the amide of formula (I) and a precipitate of dicyclohexylurea; and
(d') filtering off the dicyclohexylurea precipitate and isolating the amide of formula (I) by concentrating the filtrate, drying and repeatedly crystallizing from organic solvents.

In the step (d'), the organic solvent is preferably acetone. The molar ratio carnitine acyl-derivative: amine (or aminoacid): dicyclohexyl carbodiimide is preferably 1:1:2.

The processes A and B for preparing the amides of formula (I) are illustrated in the following synthesis scheme:

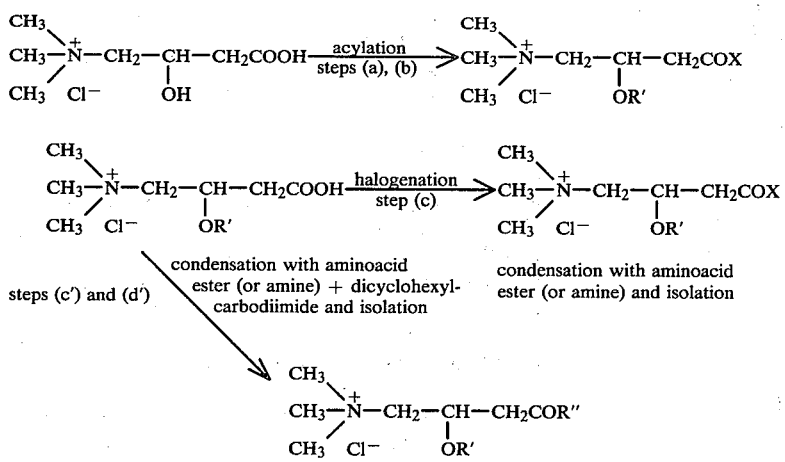

The following non-limiting examples illustrate the preparation of some of the esters and amides of the present invention.

EXAMPLE 1

Preparation of acetyl carnitine amide with taurine (Process A)

Preparation of acid chloride or acetyl carnitine hydrochloride: To a suspension of acetyl carnitine hydrochloride prepared as previously described (2 grams; 0.01 moles in 30 cc of anhydrous $CH_2Cl_2$) $PCl_5$ (2.1 grams; 0.01 moles) was added. The resulting mixture was kept under reacting conditions at room temperature and under magnetic stirring for 4 hours (the time necessary for solubilizing the acetyl carnitine). Then, the solvent was evaporated and the residue was washed with small volumes of ethyl ether for three times (30 cc) and kept under vacuum until the solvent was completely removed. The residue was used as such for the next reaction.

Preparation of acetyl carnitine amide with taurine: To a taurine solution cooled to 0° C.–5° C. (2.5 grams; 0.02 moles in water/acetone 100/150 cc containing 5 grams, 0.06 moles, of $NaHCO_3$) was dropwise added the solution in anhydrous acetone (10 cc) of the previously obtained acid chloride. The mixture was kept under reacting conditions at room temperature for 2 hours. Thereafter, the acetone was evaporated. The aqueous solution was brought to pH 2.5-3 with diluted hydrochloric acid and concentrated under vacuum till dryness. The residue was taken up with anhydrous methanol. The unsoluble products were filtered off and the filtrate was precipitated with acetone. The precipitated product was found to be the pure amide, which was crystallized from ethanol. (yield: 70).

M.P.—290°–295° C.

|  | C | H | S |
|---|---|---|---|
| Elem. An. $C_{11}H_2N_2O_6S$  calculated | 42.56 | 7.14 | 10.53 |
| found | 42.00 | 6.79 | 10.16 |

Because of the chlorine absence, an inner salt type structure is brought about:

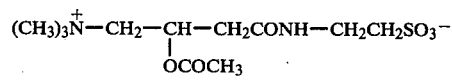

NMR: δ 8.0 (m,1H,CONH); 5.5

(m, 1H, CH);
  |
  OCO
  |
3.7

(d, 2H, $\diagdown$N—CH$_2$—);
        $\diagup$ 3.3 (m,2H,—NH—CH$_2$); 3.1 (s,9H,N (CH$_3$)$_3$); 2.9 (m,2H,—CH$_2$—SO$_3$); 2.5 (d,2H,—CH$_2$CO—); DMSO

EXAMPLE 2

Preparation of propionyl carnitine amide of leucine methyl ester

Preparation of propionyl carnitine:

Carnitine hydrochloride (1.98 g; 0.01 moles) was dissolved in 5 cc of trifluoroacetic acid and to the solution propionyl chloride (1 cc; 0.01 moles) was added. The resulting solution was kept at 40°–45° C. overnight. The solution was then cooled to room temperature and acetone (50 cc) was added thereto keeping under stirring for 2 hours. The solid precipitate which formed (carnitine) was filtered off, 30 cc of ethyl ether were added to the filtrate and the resulting mixture was kept under stirring at 0° C. The solid precipitate which formed was filtered off and crystallized with ethanol-acetone-ethyl ether.

M.P.: 158°–160° C.

| Elem. An. C₁₀H₂₀ClNO₄ | | C | H | N | Cl |
|---|---|---|---|---|---|
| | calculated | 47.34 | 7.94 | 5.52 | 13.97 |
| | found | 47.22 | 8.09 | 5.50 | 13.71 |

NMR: δ 5.69

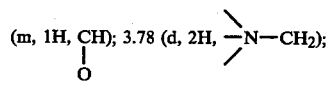

(m, 1H, CH); 3.78 (d, 2H, \N—CH₂);

3.27 (s,9H,N⁺(CH₃)₃); 2.92 (d,2H,—CH₂—CO); 2.71 (q,2H,OCOCH₂); 1.11 (t,3H,—CH₂—CH₃)D₂O

Preparation of propionyl carnitine amide of leucine methyl ester: To 1.82 grams (0.01 moles) of methyl leucinate hydrochloride 0.8 cc (0.01 moles) of pyridine in 15 cc of acetone were added. Pyridine hydrochloride precipitated, which was filtered off. To the methyl ester of leucine free base was added an aqueous solution of 2.54 grams (0.01 moles) of propionyl carnitine in 3.5 cc. Then, 4.12 grams of dicyclohexyl carbodiimide dissolved in 5 cc of acetone were slowly added under stirring to the solution. A precipitate of dicyclohexylurea formed which after 16 hours was filtered off. The mother liquors were concentrated under vacuum. The raw product thus obtained was crystallized from methanol-acetone, furnishing a solid, very hygroscopic product (yield: 75%).

| | | C | H | N | Cl |
|---|---|---|---|---|---|
| Elem. An. | calculated | 53.59% | 8.75% | 7.37% | 9.31% |
| C₁₇H₃₃O₅N₂Cl | found | 53.63% | 8.71% | 7.33% | 9.36% |

NMR: δ 5.69

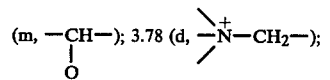

(m, —CH—); 3.78 (d, —N⁺—CH₂—);

3.78 (s, —COOCH₃); 3.27 (s,N⁺(CH₃)₃); 2.92 (d,—CH₂CO); 2.71 (d,—OCOCH₂—); 1.52 (m,—CH₂—CH) 1.11 (t,—CH₃); 0.95

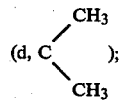

(d, C\CH₃ /CH₃);

4.52 (m,N—CH—); D₂O

EXAMPLE 3

Preparation of acetyl carnitine amide of phenylglycine ethylester (Process A)

10 grams of phenylglycine were added to 150 ml of absolute ethanol. In the resulting mixture a stream of gaseous HCl was bubbled at room temperature under stirring until all the phenylglycine was dissolved. The resulting solution was kept under stirring overnight and then cooled and evaporated under vacuum. The residue was again dissolved in water and neutralized with NaHCO₃. Phenylglycine ethylester free base was extracted with CH₂Cl₂.

To a solution of 1.8 grams (10 mmoles) of phenylglycine ethylester free base dissolved in 10 ml of CH₂Cl₂ was added a solution of acetyl carnitine chloride (10 mmoles in CH₂Cl₂). The mixture was kept under stirring overnight at 50° C. and then cooled. Upon addition of ethyl ether (50 ml) to this solution, an oil formed. The oil thus formed was dissolved in a mixture ethanol:acetone (5:1) and again precipitated with ether.

NMR (DMSO) δ=1.1 (t,—CH₂—CH₃); 2.0 (s,—CO—CH₃); 2.8 (d,—CH₂—COO—); 3.2 (s,—(CH₃)₃—N); 3.5 (d,—N—CH₂); 4.0 (q,—CH₂—CH₃);

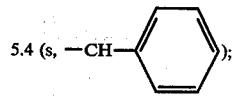

5.4 (s, —CH—⟨⟩);

5.5 (m,—CH₂—CH-CH₂—);

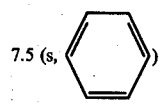

7.5 (s, ⟨⟩)

9.2 (d,CO—NH—).

| | | C | H | N | Cl |
|---|---|---|---|---|---|
| Elem. An. | calculated | 56.92 | 7.29 | 6.99 | 8.84 |
| | found | 56.84 | 7.31 | 6.89 | 8.72 |

EXAMPLE 4

Preparation of acetyl carnitine trifluoroethyl amide (Process B)

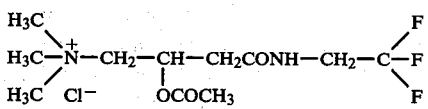

To a solution of 2,2,2-trifluoroethylamine hydrochloride (2.7 grams; 0.02 moles) in tetrahydrofuran (150 ml) and triethylamine (2.8 ml; 0.02 moles) was added acetyl carnitine chloride (4.8 grams; 0.02 moles) in water (10 ml) and lastly N,N'-dicyclohexylcarbodiimide (4.2 grams; 0.02 moles) dissolved in tetrahydrofuran (50 ml). The reaction mixture was kept for a whole day under stirring at room temperature. A precipitate formed. The precipitate consisting of dicyclohexyl urea was filtered and the filtrate was concentrated until complete removal of tetrahydrofuran. The residual aqueous solution was washed with CHCl₃ (2×50 ml), then evaporated to dryness. The raw solid was taken up with CH₃CN (30 ml), and the resulting mixture was kept at 0° C.-5° C. for 2 hours. After filtering off the unreacted acetyl carnitine, if any, upon addition of ethyl acetate-ethyl ether to the filtrate a product crystallized as a very hygroscopic solid which was stored in a nitrogen atmosphere in anhydrous conditions.

NMR δ (D₂): 2.06 (3H,s—OCOCH₃); 2.66 (2H,d-CH₂,d,—CH₂CONH—); 3.16 (9H,s, (CH₃)₃N⁺—);

3.61-4.18 (2H, m, (CH₃)₃N⁺—CH₂;

-continued

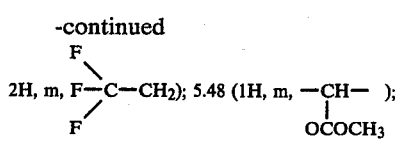

9.21 (1H,d,—CONH)

|  | | C % | H % | Cl % | F % | N % |
|---|---|---|---|---|---|---|
| Elem. An. | calculated | 41.36 | 6.70 | 11.12 | 17.68 | 8.65 |
| $C_{11}H_{20}ClF_3N_2O_3$ | found | 41.19 | 6.59 | 11.05 | 17.77 | 8.73 |

PHARMACOLOGIC EFFECTS

The pharmacologic effects of the compounds forming the subject matter of the invention were investigated by means of the following techniques:

(a) Acute Toxicity ($LD_{50}$)

The method used was that described by C. S. Weil in "Tables for convenient calculation of median-effect dose ($LD_{50}$ or $ED_{50}$) and instructions on their use", Biometrics, 249–263, 1952.

The tolerance of the compounds under investigation was studied after either i.p. or oral administration to rats. The results show that the compounds under investigation are excellently tolerated (see Table I).

(b) Inotropic effect

Rabbit hearts isolated by Langendorff's method were perfused in a Ringer solution oxygenated at 38.2° C. The isometric concentrations, ECG and coronary flow were recorded using a "Battaglia-Rangoni" polygraph.

Metabolic damage in the heart muscle was induced by removing the oxygen from the perfusion liquid until contractile force was reduced by 80%.

In these conditions of prolonged anoxia myocardial aerobic glycolysis was slowed down, accompanied by accumulation of catabolic acids due to storage of pyruvic acid and its conversion to lactic acid which cannot be utilized owing to the depression of the pyridinic enzymes, such as lacticodehydrogenase. This affects anaerobic glycolysis involving an ever increasing number of enzymes, with a progressive and increasingly more critical exhaustion of the myocardium.

Thus there is a whole series of cardiac muscle fatigue levels recorded by the pattern of the parameters taken into account i.e. contractile force, coronary output, heart rate and cardiac rhythm. As soon as the contractile force was reduced by 80%, the perfusion liquid was once again oxygenated without adding other compounds (controls) or with the addition of the compounds under investigation at various concentrations.

The contractile force of the heart was investigated and showed a positive inotropic effect at 10 minutes following interruption of the period of anoxia (restoration of the myocardium).

The results of Student's "t" test showed that the compounds under investigation induce a statistically significant positive inotropic effect versus controls. Table I illustrates the increased percentage values versus controls.

(c) Anti-arrhythmic effect

In order to evaluate by means of in vivo test the anti-arrhythmic effect exerted by the various carnitine derivatives in addition to and versus the usual in vitro tests, the method described by Nwangwu et al. (Arch. Int. Pharmacodyn., 1977, v. 229, 219) was employed.

This method is carried out by injecting a solution of aconitine into the caudal artery and recording the time of the appearance of arrhythmia and tachycardia from 2 to 60 minutes following the administration of the compounds under investigation.

Table I shows the anti-arrhythmic effect calculated by increased latency time for the onset of arrhythmias in treated animals versus controls.

(d) Effect antagonizing adrenaline

Male Albino Swiss mice weighing 12–22 g, divided into groups of 10, were treated with the compounds under investigation or with saline (controls) i.p. and then 30 minutes later with adrenaline (treated) at a dose capable of causing death in 100% of the control animals due to ventricular fibrillation and cardiac lesions ensuing from increased heart rate, pressure and oxygen consumption by the myocardium.

Mortality was monitored for 36 hours and the effect of the compounds was expressed in % of survivals versus treated animals. See Table I.

(e) Antagonism to cardiazol

Female Albino Wistar rats weighing 120–150 g. in individual cages, received the compounds under investigation (mg/kg via the oral route) and 100 mg/2 ml/kg of cardiazol 30 minutes later.

Table II shows the percentage of animals protected from death by convulsions versus controls during the 5 hours following administration.

(f) Interaction with barbiturates

Male Albino Swiss mice weighing 18–22 g divided into groups of 10 received the compounds under investigation (mg/kg via the oral route) or the vehicle (control group) and 75 mg/kg of EVIPAN 30 minutes later.

The duration of the absence of the righting reflex was measured and the difference versus the control group was calculated in percentage values. See Table II.

(g) Effect on spontaneous motility

Male Albino Swiss mice weighing 18–22 g, were divided into two groups of 5 and caged for at least 1 week. One group received the compounds under investigation and the other group (control group) was given the vehicle. The animals remained in their cages and were placed on the ANIMEX (Farad-Sweden) apparatus which recorded the movements for two 30-minute intervals beginning from 5 minutes after administration of the compounds.

Table II gives the results expressed as percentage variation in the number of spontaneous movements of the treated animals versus those of the control animals.

TABLE I

Pharmacologic activity of some Carnitine amides.
LD$_{50}$, i.p. and oral in mice, antifibrillation effect in mice, effect antagonizing adrenaline in mice and inotropic effect on isolated rabbit heart.

$(CH_3)N-CH_2-CH(OR')-CH_2-COOR'$

| | LD$_{50}$ mg/kg i.p. | LD$_{50}$ mg/kg oral | Antifibrillation Effects (mg/kg i.p. dose) % reduction | Antiadrenaline Effects (mg/kg i.p. dose) % mortality reduction | Inotropic Effect $10^{-5}$ gl$^{-1}$ dose % of controls |
|---|---|---|---|---|---|
| R' = COCH$_3$ | | | | | |
| R" = 2-sulfonyl ethyl amino | 1500 | 4000 | 70 (300) | 65 (450) | +62 |
| 2-hydroxy-3 carbethoxy propyl amino | 450 | 1300 | 65 (50) | 60 (70) | +53 |
| 1-carbomethoxy-2 methyl propyl amino | 600 | 2400 | 100 (50) | 80 (50) | +70 |
| 1-carbomethoxy-3 methyl butyl amino | 1000 | 3500 | 70 (50) | 75 (50) | +45 |
| 1-carbomethoxy-2 methyl butyl amino | 500 | 1200 | 65 (40) | 50 (100) | +45 |
| (1,2-dicarbomethoxy ethyl) amino | 1500 | 4200 | 80 (75) | 55 (300) | +48 |
| (1,3-dicarbomethoxy propyl) amino | 1000 | 3600 | 65 (20) | 40 (150) | +40 |
| R' = O—CO—CH$_2$CH$_3$ | | | | | |
| R" = 2-sulfonyl ethyl amino | 1500 | 4000 | 95 (150) | 70 (300) | +50 |
| 1-carbomethoxy-2-methyl propyl amino | 500 | 1350 | 60 (35) | 40 (50) | +65 |
| 1-carbomethoxy-3-methyl butyl amino | 600 | 2350 | 75 (50) | 70 (100) | +45 |
| 1-carbomethoxy-2-methyl butyl amino | 750 | 2500 | 65 (50) | 50 (100) | +65 |
| 1,2-dicarbomethoxy ethyl amino | 590 | 1800 | 70 (40) | 70 (100) | +50 |
| 1,3-dicarbomethoxy propyl amino | 400 | 1200 | 60 (10) | 40 (70) | +45 |
| R' = O—CO—CH$_2$—CH$_2$—CH$_3$ | | | | | |
| R" = 2-sulfonyl ethyl amino | 1500 | 4000 | 60 (50) | 50 (300) | +40 |

TABLE II

Pharmacologic activity of some Carnitine amides.
Antagonism to cardiazol in the rat; interaction with barbiturates in mice; effect on spontaneous motility in mice.

$(CH_3)N-CH_2-CH(OR')-CH_2-COOR'$

| | Antagonism to cardiazol mg/kg i.p. dose % protection from death | Barbituric interaction mg/kg i.p. dose % reduction of RR loss | Spontaneous motility (mg/kg i.p. dose) % increase versus controls (a) |
|---|---|---|---|
| R' = COCH$_3$ | | | |
| R" = 2-sulfonyl ethyl amino | 65 (150) | 30 (100) | +25 (50) |
| 2-hydroxy-3 carbethoxy propyl amino | 70 (150) | 25 (50) | +30 (50) |
| 1-carbomethoxy-2 methyl propyl amino | 84 (100) | 40 (50) | +50 (35) |
| 1-carbomethoxy-3 methyl butyl amino | 60 (150) | 35 (50) | +28 (25) |
| 1-carbomethoxy-2 methyl butyl amino | 53 (100) | 35 (40) | +34 (25) |
| (1,2-dicarbomethoxy ethyl) amino | 75 (50) | 20 (75) | +60 (50) |
| (1,3-dicarbomethoxy propyl) amino | 70 (50) | 40 (20) | +19 (25) |
| R' = O—CO—CH$_2$CH$_3$ | | | |
| R" = 2-sulfonyl ethyl amino | 40 (150) | 60 (100) | +40 (50) |
| 1-carbomethoxy-2-methyl propyl amino | 38 (35) | 58 (50) | +75 (25) |
| 1-carbomethoxy-3-methyl butyl amino | 32 (50) | 31 (100) | +62 (50) |
| 1-carbomethoxy-2-methyl butyl amino | 39 (50) | 27 (100) | +35 (100) |
| 1,2-dicarbomethoxy ethyl amino | 51 (40) | 25 (100) | +59 (25) |
| 1,3-dicarbomethoxy propyl amino | 47 (50) | 50 (50) | +25 (50) |
| R' = O—CO—CH$_2$—CH$_2$—CH$_3$ | | | |
| R" = 2-sulfonyl ethyl amino | 58 (50) | 70 (50) | +43 (50) |

RR = righting reflex; mean monitoring time = 48 min.
(a) = control value: 850 ± 65 in 30 min. of experiment (5 mice per cage)

The compounds of the present invention are orally or parenterally administered, in any of the usual pharmaceutical forms which are prepared by conventional procedures well-known to those persons skilled in the pharmaceutical technology. These forms include solid and liquid oral unit dosage forms such as tablets, capsules, solutions, syrups and the like as well as injectable forms, such as sterile solutions for ampoules and phials.

For these pharmaceutical forms the usual solvents, diluents and excipients are used. Optionally, sweetening, flavoring and preservative agents can also be present. Non limiting examples of such agents are sodium carboxymethylcellulose, polysorbate, mannitol, sorbitol, starch, avicel, talcum and other agents which will be apparent to those skilled in the pharmaceutical technology.

The dose which is administered will be determined by the attending physician having regard to the age, weight and general conditions of the patient, utilizing sound professional judgement. Although effective results can be noticed at doses as low as 5 to 8 mg/kg of body weight daily, a dose of from about 10 to about 50 mg/kg of body weight is preferred. Whenever necessary, larger doses can be safely administered in view of the low toxicity of the compounds of this invention.

As non-limiting examples and depending on the specific pharmaceutical form of administration, the following dosages can be indicated:
- for the phials: from 5 to 500 mg
- for the capsules: from 15 to 50 mg
- for the tablets: from 15 to 500 mg
- for the oral solutions: from 15 to 50 mg

What is claimed is:

1. An amide of an acyl-carnitine represented by the formula (I)

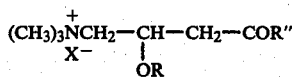

wherein X$^-$ is a halogen anion; R is acetyl; halogen-substituted acetyl; propionyl; halogen-substituted propionyl; butyryl; halogen-substituted butyryl; isobutyryl;

β-hydroxy butyryl; acetoacetyl, linoleyl or pantothenyl; and R" is amino provided that R is not acetyl, propionyl or butyryl, or R" is 2-sulfonyl-ethylamino, (2-hydroxy-3-carbethoxy-propyl) amino, (1-carbomethoxy-2-methyl-propyl) amino, (1-carbomethoxy-3-methyl-n-butyl) amino, (1-carbomethoxy-2-methyl-n-butyl) amino, (1,2-dicarbomethoxy-ethyl) amino, (1,3-dicarbomethoxy-propyl) amino, (2-carbethoxy-benzyl) amino, (4-carbethoxy-phenyl) amino, 2-mercapto-1-carbomethoxy-ethyl) amino, 2-mercaptoethyl amino, (5-trimethyl ammomonium chloride-1-carbethoxy pentyl) amino, (carbethoxy methyl) amino or (carbethoxy ethyl) amino radical.

2. An amide according to claim 1 wherein said halogen-substituted acetyl is chloro-acetyl, dichloro-acetyl or bromo-acetyl; said halogen-substituted propionyl is bromopropionyl and said halogen-substituted butyryl is chlorobutyryl.

3. An amide of an acyl-carnitine represented by the formula (I)

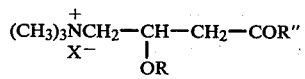

wherein X⁻ is a halogen anion; R is halogen-substituted acetyl, halogen-substituted propionyl, halogen-substituted butyryl, linoleyl or pantothenyl; and R" is amino, 2-sulfonyl-ethylamino, (2-hydroxy-3-carbethoxy-propyl) amino, (1-carbomethoxy-2-methylpropyl) amino, (1-carbomethoxy-3-methyl-n-butyl) amino, (1-carbomethoxy-2-methyl-n-butyl) amino, (1,2-dicarbomethoxy-ethyl) amino, (1,3-dicarbomethoxy-propyl) amino, (2-carbethoxy-benzyl) amino, (4-carbethoxy-phenyl) amino, 2-mercapto-1-carbomethoxy-ethyl) amino, 2-mercaptoethyl amino, (5-trimethyl ammomonium chloride-1-carbethoxy pentyl) amino, (carbethoxy methyl) amino or (carbethoxy ethyl) amino radicals.

4. An amide of an acyl-carnitine represented by the formula (I)

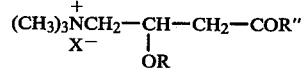

wherein X⁻ is a halogen anion; R is acetyl; halogen-substituted acetyl; propionyl; halogen-substituted propionyl, butyryl; halogen-substituted butyryl; isobutyryl; β-hydroxy butyryl; acetoacetyl, linoleyl or pantothenyl; and R" is 2-sulfonyl-ethylamino, (2-hydroxy-3-carbethoxy-propyl) amino, (1-carbomethoxy-2-methylpropyl) amino, (1-carbomethoxy-3-methyl-n-butyl) amino, (1-carbomethoxy-2-methyl-n-butyl) amino, (1,2-dicarbomethoxy-ethyl) amino, (1,3-dicarbomethoxy-propyl) amino, (2-carbethoxy-benzyl) amino, (4-carbethoxy-phenyl) amino, 2-mercapto-1-carbomethoxy-ethyl) amino, 2-mercaptoethyl amino, (5-trimethyl ammomonium chloride-1-carbethoxy pentyl) amino, (carbethoxy methyl) amino or (carbethoxy ethyl) amino radicals.

5. A composition for the treatment of functional arrhythmias, arrythmias secondary to myocardial-sclerotic diseases and barbiturate-induced depressions and for use as psychostimulant which comprises an amide of formula (I) as defined in claim 1 in a pharmaceutically effective amount and a pharmacologically acceptable excipient.

6. A composition according to claim 5 in unit dosage form comprising from about 5 to about 500 mg of said amide.

7. A method of treating depression comprising administering to a patient afflicted by depression an amide of formula (I) as defined in claim 1 in an amount effective in the treatment of depression.

* * * * *